(12) United States Patent
Rautenstrauch et al.

(10) Patent No.: US 6,878,852 B2
(45) Date of Patent: Apr. 12, 2005

(54) PROCESS FOR HYDROGENATION OF CARBONYL AND IMINOCARBONYL COMPOUNDS USING RUTHENIUM CATALYSTS COMPRISING TETRADENTATE DIIMINO-DIPHOSPHINE LIGANDS

(75) Inventors: Valentin Rautenstrauch, Collonges-sous Saleve (FR); Raphaël Churlaud, Le Mans (FR); Robert Harold Morris, Toronto (CA); Kamaluddin Abdur-Rashid, Mississauga (CA)

(73) Assignee: Firmenich SA, Geneva (CH)

( * ) Notice: Subject to any disclaimer, the term of this patent is extended or adjusted under 35 U.S.C. 154(b) by 0 days.

(21) Appl. No.: 10/415,086

(22) PCT Filed: Nov. 11, 2001

(86) PCT No.: PCT/IB01/02166

§ 371 (c)(1),
(2), (4) Date: Apr. 25, 2003

(87) PCT Pub. No.: WO02/40155

PCT Pub. Date: May 23, 2002

(65) Prior Publication Data

US 2004/0015017 A1 Jan. 22, 2004

(30) Foreign Application Priority Data

Nov. 17, 2000 (WO) ................................. PCT/IB00/01693

(51) Int. Cl.[7] ............................ B01J 31/24; B01J 31/18; C07C 29/136; C07C 209/52; C07F 15/00
(52) U.S. Cl. ...................... 568/881; 568/814; 568/850; 568/861; 568/862; 568/863; 568/864; 568/874; 568/878; 568/885
(58) Field of Search .............................. 568/814, 850, 568/861–864, 874, 878, 881, 885

(56) References Cited

FOREIGN PATENT DOCUMENTS

EP  1 120 162 A2  12/1997

OTHER PUBLICATIONS

Wong et al., Polyhedron (1996), 15(21), p. 3905–3907.*
Wong et al., Polyhedron (1997), 16(3), p. 433–439.*
Abstract—XP002175802, Jingxing et al., "Preparation of chiral diaminodiphosphine metal complexes as catalysts in asymmetrically catalytic hydrogenation", STN 2000.
Abstract—XP002175800, Wai–Kwok et al., Synthesis and characterizations of chiral diimino–and diaminodiphosphine complexes of ruthenium x–ray crystal structure of trans–RuCl2(1R, 2R–cyclohexyl–P2N2.cntdot, STN 1996.
Abstract—XP002175801, Pinapian et al. Synthesis and hydrogenation activity of diiminodiphosphine ruthenium complex RuCl2P2N2, STN 1997.
Abstract—XP002175803, Jingxing et al., Synthesis and hydrogenation properties of polydentate diiminodiphosphine ruthenium (I) complexes retrieved from STN 1995.
Abstract—XP002175805 Jingxing et al., new chiral catalysts for reduction of ketones retrieved from STN 2000.
Abstract—XP002175804 Jingxing et al., Asymmetric transfer hydrogenation of prochiral ketones catalyzed by chiral ruthenium complexes with aminophosphine ligands retrieved from STN 1999.
Abstract—XP002175799 Jingxing et al., Homogeneous catalysis hydrogenation of functional zed olefins by diaminodiphosphineruthenium (II) 1995.
Abstract—XP001021059, Noyori et al. Chapter 6.1 Hydrogenation of Carbonyl Groups, vol. 1 pp. 199–246 (1999).

\* cited by examiner

Primary Examiner—Brian Davis
(74) Attorney, Agent, or Firm—Winston & Strawn LLP

(57) ABSTRACT

A process for the hydrogenation, using molecular hydrogen ($H_2$) of a catalytic system, wherein the catalytic system includes a base and a complex of formula (II):

$$Ru(P_2N_2)Y_2 \qquad (II)$$

wherein Y represent simultaneously or independently a hydrogen or halogen atom, a hydroxy group, or an alkoxy, carboxyl or other anionic radical, and $P_2N_2$ is a tetradentate diimino-diphosphine ligand.

19 Claims, No Drawings

PROCESS FOR HYDROGENATION OF CARBONYL AND IMINOCARBONYL COMPOUNDS USING RUTHENIUM CATALYSTS COMPRISING TETRADENTATE DIIMINO-DIPHOSPHINE LIGANDS

CROSS-REFERENCE TO RELATED APPLICATIONS

This application is a 371 filing of International Application PCT/IB01/02166 filed Nov. 16, 2001, which claims the benefit of International Application PCT/IB00/01693 filed Nov. 17, 2000.

TECHNICAL FIELD

The present invention relates to the field of catalytic hydrogenations, using $H_2$, and more particularly to the use of a catalytic system comprising a base and a ruthenium complex with a tetradentate diimino-diphosphine ($P_2N_2$) ligand in hydrogenation processes for the reduction of compounds containing a carbon-heteroatom double bond.

PRIOR ART

Reduction of carbon-heteroatom double bonds such as ketones, aldehydes or imines, is one of the fundamental reactions in chemistry, and is used in a large number of chemical processes.

Amongst the several different kinds of processes known to achieve such transformation, two important types are:
a) the hydrogen transfer processes, in which hydrogen-donors such as secondary alcohols, and in particular isopropanol ($^iPrOH$), are used;
b) the hydrogenation processes, in which molecular hydrogen is used.

Both hydrogen transfer and hydrogenation processes need a catalyst or catalytic system to activate the reducing agent, namely an alcohol or molecular hydrogen respectively.

From a practical point of view, hydrogenation processes are more attractive than hydrogen transfer processes as they use inexpensive hydrogen gas and can be run in the presence of a small quantity or even in the absence of a solvent, in contrast to the hydrogen transfer processes, which need large volumes of solvent as reductant. However the hydrogenation processes imply the activation of molecular hydrogen, which is more difficult to achieve than the activation of an alcohol.

Amongst the potentially interesting catalysts reported in the prior art to activate molecular hydrogen, there are the ruthenium complexes with tetradentate diamino-diphosphino ($P_2(NH)_2$) ligands, hereinafter referred to as "$Ru/P_2(NH)_2$ complexes" unless specified otherwise (e.g. see Gao et al. in Tianranqi Huagong, 1995, 20, 1 or CN 1047597 C) and the analogous ruthenium complexes with tetradentate diimino-diphosphine ($P_2N_2$) ligands, hereinafter referred to as "$Ru/(P_2N_2)$ complexes" unless specified otherwise (e.g. see Xu et al. in Yingyong Huaxue 1997, 14, 58 or Gao et al. in Chirality, 2000, 12, 383).

However, the reported processes, using these two types of complexes, have some drawbacks. Indeed, on the one hand, the results reported in the prior art for such processes show that the performance of the $Ru/(P_2N_2)$ complexes were always substantially inferior to those of the $Ru/P_2(NH)_2$ complexes, creating thus a prejudice for the use of the former as efficient catalysts for the reduction of carbon-heteroatom double bond. On the other hand, the inconvenience of using the $Ru/P_2(NH)_2$ complexes lies in the synthesis of the $P_2(NH)_2$ ligands which requires an expensive, and industrially delicate step of reduction of the diimino-diphosphine precursor ($P_2N_2$) using a metal hydride salt.

DESCRIPTION OF THE INVENTION

In order to overcome the problems aforementioned, the present invention relates to new processes for the reduction by molecular hydrogen ($H_2$) of compounds containing a carbon-heteroatom double bond wherein a base and a ruthenium complex with a tetradentate diimino-diphosphine ($P_2N_2$) ligand are usefully used as the catalytic system. Indeed, these processes have surprisingly proved to be at least as effective as the ones wherein the $Ru/P_2(NH)_2$ complexes are used.

More precisely, the invention concerns a process for the hydrogenation, using molecular hydrogen ($H_2$), of a C=O or C=N double bond of a substrate, to the corresponding hydrogenated compound, in the presence of a catalytic system, comprising a base and a ruthenium complex with a tetradentate diimino-diphosphine ($P_2N_2$) ligand.

In the process of the invention, there can be reduced substrates of formula

(I)

in which W is an oxygen atom or a NR group, R being a hydrogen atom, a hydroxy radical, a $C_1$ to $C_8$ cyclic, linear or branched alkyl or alkenyl group, possibly substituted, or an aromatic ring, possibly substituted; and $R^a$ and $R^b$ represent simultaneously or independently a hydrogen, an aromatic group possibly substituted, a cyclic, linear or branched alkyl or alkenyl group, possibly substituted, or a heterocyclic group possibly substituted; or two of symbols $R^a$, $R^b$ and R taken together form a ring, possibly substituted,
to provide the corresponding hydrogenated compounds of formula

(I')

wherein W, $R^a$ and $R^b$ are defined as in formula (I).

Possible substituents of $R^a$, $R^b$ and R are halogen atoms, $OR^c$, $NR^c_2$ or $R^c$ groups, in which $R^c$ is a hydrogen atom or a $C_1$ to $C_{10}$ cyclic, linear or branched alkyl or alkenyl group.

Since $R^a$ and $R^b$ may be different, it is hereby understood that the final product, of formula (I'), may be chiral, thus possibly consisting of a practically pure enantiomer or of a mixture of stereoisomers, depending on the nature of the catalyst used in the process.

Preferred substrates are imines (W=NR) or ketones/aldehydes (W=O) that will provide respectively an amine or an alcohol, which are useful in the pharmaceutical, agrochemical or perfumery industries as final product or as an intermediate.

Particularly preferred substrates are the ketones or aldehydes that will provide an alcohol, which are useful in the perfumery industries as final product or as an intermediate. Also particularly preferred substrates are the imines that will provide an amine, which are useful in the pharmaceutical or agrochemical industries as final product or as an intermediate.

The processes of the invention are characterized by the use of a catalytic system comprising a ruthenium complex with tetradentate diimino-diphosphine ($P_2N_2$) ligands and a base.

Useful complexes are of the general formula $$[Ru(P_2N_2)Y_2] \quad (II)$$

in which the Y symbols represent, simultaneously or independently, a hydrogen or halogen atom, a hydroxyl radical, or a $C_1$ to $C_8$ alkoxy or acyloxy or amido radical or other anionic radical, and the ligand $P_2N_2$ represents a tetradentate ligand of formula

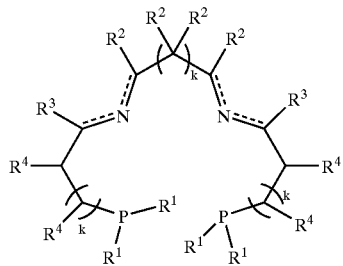

(III)

in which the dotted lines indicate the position of a C=N double bond;

the $R^1$ symbols, taken separately, represent simultaneously or independently a linear or branched alkyl or alkenyl group containing 1 to 8 carbon atoms, possibly substituted, a cycloalkyl radical or an aromatic ring, possibly substituted; or two $R^1$ groups bonded to the same P atom being bonded together to form a ring having 5 to 8 atoms and including the phosphorous atom to which said $R^1$ groups are bonded;

$R^2$, $R^3$ and $R^4$, taken separately, represent simultaneously or independently a hydrogen atom, a linear or branched alkyl or alkenyl group containing 1 to 8 carbon atoms, possibly substituted, a cycloalkyl radical or an aromatic ring, possibly substituted; or two adjacent or geminal $R^2$ groups being bonded together to form a ring including the carbon atom to which said $R^2$ groups are bonded; or a $R^3$ group and a $R^2$ group, in α-position to the same N atom, being bonded together to form a ring; or two adjacent $R^4$ groups being bonded together to form an aromatic ring; and indices k are, simultaneously or independently, equal to 0 or 1.

Possible substituents of $R^1$, $R^2$, $R^3$ and $R^4$ being halogen atoms or $C_1$ to $C_6$ alkyl or alkoxy groups.

Preferably, the ligand $P_2N_2$ in formula (II) represents a compound of formula

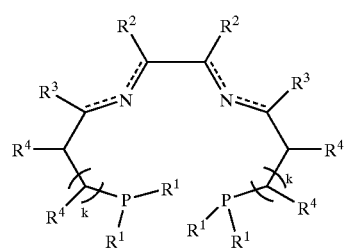

(IV)

wherein the dotted lines indicate the position of a C=N double bond;

the $R^1$ symbols, taken separately, represent simultaneously or independently a linear or branched alkyl group containing 1 to 4 carbon atoms, a cycloalkyl radical or an aromatic ring, possibly substituted; or two $R^1$ groups bonded to the same P atom being bonded together to form a ring having 5 to 6 atoms and including the phosphorous atom to which said $R^1$ groups are bonded;

$R^2$, $R^3$ and $R^4$, taken separately, represent simultaneously or independently a hydrogen atom, a linear or branched alkyl group containing 1 to 4 carbon atoms, a cycloalkyl radical or an aromatic ring, possibly substituted; or two $R^2$ groups being bonded together to form a ring including the carbon atom to which said $R^2$ groups are bonded; or two adjacent $R^4$ groups being bonded together to form an aromatic ring; and indices k are, simultaneously or independently, equal to 0 or 1.

Possible substituents of the aromatic rings are $C_1$ to $C_4$ alkyl or alkoxy groups or fluorine or chlorine atoms.

The processes of the invention are particularly attractive when are used complexes of the formula (II) $[Ru(P_2N_2)Y_2]$ wherein the Y symbols represent, independently or simultaneously, a hydrogen, a chlorine atom, a methoxy, ethoxy or isopropoxy radical, or a $CH_3COO$ or $CH_3CH_2COO$ radical; and the ligand $P_2N_2$ represents a ligand of the formula

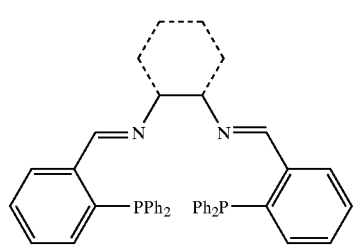

(V)

wherein the dotted lines represent an optional $C_6$ aliphatic ring and Ph represents a possibly substituted phenyl radical. Possible substituents of the phenyl radical are methyl or methoxy groups or fluorine atoms.

As can be seen from formulae (III) to (V), the ligands $P_2N_2$ may be chiral or achiral. Whenever $P_2N_2$ is chiral, the process of the invention can be useful in asymmetric hydrogenation. In this respect, we have surprisingly observed that, when complexes of formula (II) with a chiral ligand are used in the process of the invention, the chirality of the final product is the opposite of the one described in the prior art for transfer hydrogenation processes (e.g. see Gao et al. in Chirality, 2000, 12, 383).

Many of the ligands described above are known in the state of the art, and, unless specified differently in the examples, they are obtained according to the methods described in the literature. Some references are cited in the examples.

In a general way, the complexes of formula (II) can be prepared and isolated prior to their use in the process according to the general methods described in the literature (e.g. see Xu et al. in Yingyong Huaxue 1997, 14, 58)

Moreover, the complexes can be prepared in situ, by several methods, in the hydrogenation medium, without isolation or purification, just before their use.

One of the possible procedures to advantageously prepare in situ a complex of formula (II) consists in reacting an appropriate Ru complex of formula

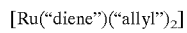

in which "diene" represents a cyclic or linear hydrocarbon containing two carbon-carbon double bonds, conjugated or not, such as for example 1,5-cyclooctadiene (COD) or 1,3-butadiene, and "allyl" represents a linear or branched $C_3$ to $C_8$ hydrocarbon radical containing one carbon-carbon double bond such as for example allyl ($CH_2CHCH_2$) or methylallyl ($CH_2CCH_3CH_2$),
with a non-coordinating acid such as $HBF_4Et_2O$, preferably one equivalent with respect to the metal, and then treating the resulting solution with the required amount of a ligand $P_2N_2$ such as defined previously, and finally treating the thus obtained mixture with a base in the presence of a primary or secondary alcohol.

Preferably the [Ru(diene)(allyl)$_2$] is [Ru(COD)(allyl)$_2$] or [Ru(COD)(2-methylallyl)$_2$].

Another procedure to advantageously prepare in situ a complex of formula (II) consists in reacting a ruthenium complex of formula [Ru($C_6H_6$)(Cl)$_2$]$_2$ with a required amount of ligand $P_2N_2$, as defined previously, and then treating the thus obtained reaction mixture with a base, in the presence of an alcohol.

In any case, and independently of the procedure chosen to prepare the complex in situ, the base used is, preferably, the same base used in the process of the invention.

As previously mentioned, the catalytic system characterizing the process of the instant invention comprises a base. The use of a base provides the surprising result of increasing the activity of the Ru/($P_2N_2$) complex used in the process of the invention, allowing thus said complex to be at least as effective as the corresponding Ru/$P_2$(NH)$_2$ complex, contrary to the teaching of the prior art.

Said base can be the substrate itself, if the latter is basic, or any conventional base. One can cite, as non-limiting examples, organic non-coordinating bases such as DBU, an alkaline or alkaline-earth metal carbonate, a carboxylate salt such as sodium or potassium acetate, or an alcoholate or hydroxide salt. Preferred bases are the alcoholate or hydroxide salts selected from the group consisting of the compounds of formula ($R^8O$)$_2$M' and $R^8$OM", wherein M' is an alkaline-earth metal, M" is an alkaline metal and $R^8$ stands for hydrogen or a $C_1$ to $C_6$ linear or branched alkyl radical.

A typical process implies the mixture of the substrate with a ruthenium complex of formula (II) and a base, possibly in the presence of a solvent, and then treating such a mixture with molecular hydrogen at a chosen pressure and temperature.

The complexes of formula (II) can be added to the reaction medium in a large range of concentrations. As non-limiting examples, one can cite as complex concentration values those ranging from 0.1 ppm to 50000 ppm, relative to the amount of substrate, thus representing respectively a substrate/complex (S/com) ratio of $10^7$ to 20.

Preferably, the complex concentration will be comprised between 0.1 and 1000 ppm, i.e. a S/com ratio of $10^7$ to 1000 respectively. More preferably, there will be used concentrations in the range of 0.5 to 100 ppm, corresponding to a S/com ratio of $2\times10^6$ to 10000 respectively. It goes without saying that the optimum concentration of complex will depend on the nature of the latter and on the pressure of $H_2$ used during the process.

Useful quantities of base, added to the reaction mixture, may be comprised in a relatively large range. One can cite, as non-limiting examples, ranges between 1 and 50000 molar equivalents relative to the complex (e.g. base/com=1 to 50000), preferably 100 to 20000, and even more preferably between 400 and 10000 molar equivalents. However, it should be noted that it is also possible to add a small amount of base (e.g. base/com=1 to 3) to achieve high hydrogenation yields.

The hydrogenation reaction can be carried out in the presence or absence of a solvent. When a solvent is required or used for practical reasons, then any solvent current in hydrogenation reactions can be used for the purposes of the invention. Non-limiting examples include aromatic solvents such as benzene, toluene or xylene, hydrocarbon solvents such as hexane or cyclohexane, ethers such as tetrahydrofuran, or yet primary or secondary alcohols, or mixtures thereof. A person skilled in the art is well able to select the solvent most convenient in each case to optimize the hydrogenation reaction, however primary or secondary alcohols such as ethanol or isopropanol are the preferred solvent.

In the hydrogenation process of the invention, the reaction can be carried out at a $H_2$ pressure comprised between $10^5$ Pa and $80\times10^5$ Pa (1 to 80 bar). Again, a person skilled in the art is well able to adjust the pressure as a function of the catalyst load and of the dilution of the substrate in the solvent. As examples, one can cite typical pressures of 1 to $40\times10^5$ Pa (1 to 40 bar).

The temperature at which the hydrogenation can be carried out is comprised between 0° C. and 100° C., more preferably in the range of between 20° C. and 60° C. Of course, a person skilled in the art is also able to select the preferred temperature as a function of the melting and boiling point of the starting and final products.

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave. $H_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $C_6D_6$ unless indicated otherwise. Chemical shifts are listed in ppm.

EXAMPLE 1

General Procedure for the Catalytic Hydrogenation of Ketones and Aldehydes With the Complexes [Ru($P_2N_2$)$Y_2$] or [Ru($P_2$(NH)$_2$)$Y_2$]

A typical experiment was as follows:

A 0.002 M solution of the complex [RuCl$_2$((R,R)-cyP$_2$(NH)$_2$)] was prepared by dissolving 9.9 mg (0.01 mmol) of the complex in 5 ml of $CH_2Cl_2$.

A 0.18 M solution of $^i$PrOK was prepared by dissolving 202 mg (1.8 mmol) $^t$BuOK in 10 ml iPrOH.

The glass insert of an autoclave was charged with 7.2 ml $^{i}$PrOH and 10 μl of the 0.18 M solution of $^{i}$PrOK (1.8×10$^{-3}$ mmol). Then, to this mixture were added 2.4 g of acetophenone(20 mmol) and 10 μl of the 0.002 M complex solution (2×10$^{-5}$ mmol), resulting thus in a reaction mixture having a complex/base/substrate ratio of 1:90:10$^{6}$ (1 ppm of complex).

The charged insert was placed inside the autoclave, which was sealed and pressurized with 45 bar of H$_2$, and its contents magnetically stirred and heated to 60° C.

Samples for analysis by GC were withdrawn after taking the autoclave out of the heating bath and degassing via septum and syringe.

The septum was placed against a strong H$_2$ countercurrent over the outlet of the valve and then allowed the syringe needle to enter and to reach the bottom of the glass insert. The autoclave was then repressurized with H$_2$ and the hydrogenation reaction continued. All of the runs were carried out in the same manner.

Reactants, quantities and results are listed in Table 1.

TABLE 1

Hydrogenation of a substrate using [Ru(P$_2$N$_2$)Y$_2$]

| Test | Sub. | Complex | Com/base | Yield/time |
|---|---|---|---|---|
| 1 | 1 | [Ru((R,R)-cyP$_2$N$_2$)Cl$_2$] | 100/9000 | 100$^{a)}$/1.5 h |
| 2 | 1 | [Ru(ethP$_2$N$_2$)Cl$_2$] | 10/4500 | 97/3 h |
| 3 | 1 | [Ru(ethP$_2$N$_2$)(OAc)$_2$] | 10/50 | 100/3 h |
| 4 | 2 | [Ru(ethP$_2$N$_2$)(OAc)$_2$] | 10/4500 | 95/22 h |
| 5 | 2 | [Ru(ethP$_2$N$_2$)(OAc)$_2$] | 100/500 | 26/24 h |
| 6 | 2 | [Ru(ethP$_2$N$_2$)(OAc)$_2$] | 100/4500 | 100/3 h |
| 7 | 3 | [Ru(ethP$_2$N$_2$)(OAc)$_2$]* | 10/5000 | 55/3 h 88/20 h |
| 8 | 3 | [Ru(ethP$_2$N$_2$)(OAc)$_2$]* | 100/500 | 90/3 h |
| 9 | 3 | [Ru(ethP$_2$N$_2$)(OAc)$_2$]* | 100/5000 | 94/3 h |

$^{a)}$the product had an ee of 20%, the enantiomer R being the predominant one.
*the concentration of the substrate during the reaction was 3.1 M.
Sub.: substrate: 1) acetophenone; 2) (+)-3,3-dimethyl-5-(2',2',3'-trimethyl-3'-cyclopenten-1'-yl)-4-penten-2-one; 3) (E)-2-ethyl-4-(2,2,3-trimethyl-3-cyclopenten-1'-yl)-2-buten-1-al.
Com/base: complex/base molar ratio in ppm relative to the substrate
Yield/time = Yield (analyzed by GC or by isolation) of the corresponding alcohol (namely 1-phenyl-1-ethanol, (+)-3,3-dimethyl-5-(2',2',3'-trimethyl-3'-cyclopenten-1'-yl)-4-penten-2-ol, (E)-2-ethyl-4-(2,2,3-trimethyl-3'-cyclopenten-1'-yl)-2-buten-1-ol, respectively) after the indicated reaction time in hours.
Note:
the C=C double bonds of the starting materials have not been touched by the reduction process.

TABLE 2

Structures and names of the ligands P$_2$N$_2$
of the complexes listed in Table 1

Ligand: structure (R,R)-cyP$_2$N$_2$:

ethP$_2$N$_2$:

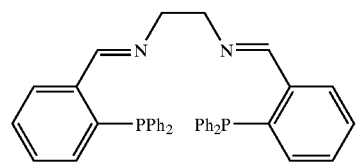

Ligands (R,R)-cyP$_2$N$_2$ were obtained according to W.-K. Wong et al. in Polyhedron, 1996, 15, 4447.

Ligand ethP$_2$N$_2$ was obtained according to J. C. Jeffery et al. in Inorg. Chem. 1980, 19, 3306.

Complex [Ru((R,R)-cyP$_2$N$_2$)Cl$_2$] was prepared as previously described by J.-X. Gao et al. in Organometallics, 1996, 15, 1087.

Complexes [Ru(ethP$_2$N$_2$)(AcO)$_2$] and [Ru(ethP$_2$N$_2$)Cl$_2$] have been obtained according to W.-K. Wong et al. in Polyhedron 1993, 12, 1415

EXAMPLE 2

Comparison Between the Performances of the [Ru(P$_2$N$_2$)Y$_2$] Complexes and Their [Ru(P$_2$(NH)$_2$)Y$_2$] Analogues a) By using a general procedure similar to that described in example 1), the [Ru((R,R)-cyP$_2$N$_2$)Cl$_2$] complexes and its [Ru((R,R)-cyP$_2$(NH)$_2$)Cl$_2$] analogue have been tested under the same conditions for the hydrogenation of acetophenone. Reactants, quantities and results are listed in Table 3.

TABLE 3

Comparison of the performances, for the hydrogenation of acetophenone, of [Ru(P$_2$N$_2$)Y$_2$] and their [Ru(P$_2$(NH)$_2$)Y$_2$] analogues

| Test | Complex | Com/base | Yield/time | (e.e.) |
|---|---|---|---|---|
| 1 | [Ru((R,R)-cyP$_2$N$_2$)Cl$_2$] | 10/900 | 100/3 h | 18 (R) |
| 2 | [Ru((R,R)-cyP$_2$(NH)$_2$)Cl$_2$]$^{1)}$ | 10/900 | 3/3 h 100/24 h | 20 (R) |
| 3 | [Ru((R,R)-cyP$_2$N$_2$)Cl$_2$] | 10/45000 | 100/3 h | 18 (R) |
| 4 | [Ru((R,R)-cyP$_2$(NH)$_2$)Cl$_2$] | 10/45000 | 100/3 h | 20 (R) |
| 5 | [Ru((R,R)-cyP$_2$N$_2$)Cl$_2$] | 100/45000 | 100/3 h | 23 (R) |
| 6 | [Ru((R,R)-cyP$_2$(NH)$_2$)Cl$_2$] | 100/45000 | 95/3 h | 17 (R) |
| 7 | [Ru((R,R)-cyP$_2$N$_2$)Cl$_2$] | 100/450000 | 100/1.5 h | 18 (R) |
| 8 | [Ru((R,R)-cyP$_2$(NH)$_2$)Cl$_2$] | 100/450000 | 86/3 h | 18 (R) |

Com/base: complex/base molar ratio in ppm relative to the substrate
Yield/time = Yield (analyzed by GC or by isolation) of the corresponding alcohol (namely 1-phenyl-1-ethanol) after the indicated reaction time in hours.
ee in % with R or S identifying the predominant enantiomer.

1) (R,R)-cyP₂(NH)₂:

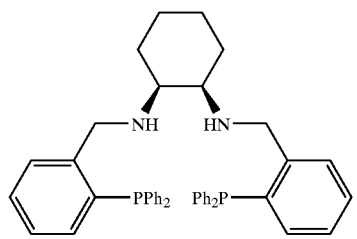

Ligand (R,R)-cyP₂(NH)₂ was obtained according to W.-K. Wong et al. in Polyhedron, 1996, 15, 4447.

Complex [Ru((R,R)-cyP₂(NH)₂)Cl₂] was prepared as previously described by J. X. Gao, et al. in Organometallics, 1996, 15, 1087.

b) Under an atmosphere of hydrogen gas (1–3 atm) at room temperature, catalytic amounts of the [Ru(P₂N₂)Y₂] or [Ru(P₂(NH)₂)Y₂] complex, together with 3–10 equivalents of KO$^i$Pr or KO$^t$Bu effectively and readily catalyzed the hydrogenation of the neat ketones or imines to the corresponding alcohol or amine respectively. A general procedure for a catalytic run is as follows:

1 to 8 g of the substrate, or its solution in 1–2 ml of $C_6D_6$, were added under a flow of hydrogen gas to a Schlenk flask containing the desired amount of catalyst and of base (KO$^i$Pr or KO$^t$Bu). The flask was then cooled to liquid nitrogen temperature, filled with $H_2$ gas, closed and allowed to gradually warm to room temperature to reach an initial $H_2$ pressure of about 3 atm. The mixture was vigorously stirred for 12 to 30 hours. Then, the catalyst was oxidized and precipitated from the alcohols or amines by the addition of hexanes in the air and then removed by filtration through a 5 mm thick pad of silica gel. The hexanes were evaporated to yield the pure alcohol. A sample was dissolved in $C_6D_6$ to determine the yield by $^1H$ NMR. Typical conditions and results are listed in Table 5.

TABLE 5

Comparison of the performances of [Ru((R,R)-cyP₂N₂)HCl] and its [Ru((R,R)-cyP₂(NH)₂)HCl] analogue as catalyst for the hydrogenation of various substrates

| Test | Sub. | Complex | Com/base | Yield/time |
|---|---|---|---|---|
| 1 | 1 | [Ru((R,R)-cyP₂N₂)HCl][1] | 500/2500 | 100/12 h |
| 2 | 1 | [Ru((R,R)-cyP₂(NH)₂)HCl][2] | 500/2500 | 100/12 h |
| 3 | 2 | [Ru((R,R)-cyP₂N₂)HCl] | 2000/10000 | 100/12 h |
| 4 | 2 | [Ru((R,R)-cyP₂(NH)₂)HCl] | 2000/10000 | 100/12 h |
| 5 | 3 | [Ru((R,R)-cyP₂N₂)HCl] | 2000/10000 | 100/12 h |
| 6 | 3 | [Ru((R,R)-cyP₂(NH)₂)HCl] | 2000/10000 | 100/12 h |
| 7 | 4 | [Ru((R,R)-cyP₂N₂)HCl] | 330/1650 | 100/4 h |
| 8 | 4 | [Ru((R,R)-cyP₂(NH)₂)HCl] | 330/1650 | 100/4 h |
| 9 | 5 | [Ru((R,R)-cyP₂N₂)HCl] | 660/3300 | 100/36 h |
| 10 | 5 | [Ru((R,R)-cyP₂(NH)₂)HCl] | 660/3300 | 100/36 h |
| 11 | 6 | [Ru((R,R)-cyP₂N₂)HCl] | 3200/22600 | 100/12 h |
| 12 | 6 | [Ru((R,R)-cyP₂(NH)₂)HCl] | 3200/22600 | 100/30 h |
| 13 | 7 | [Ru((R,R)-cyP₂N₂)HCl] | 270/1900 | 100$^a$/12 h |
| 14 | 7 | [Ru((R,R)-cyP₂(NH)₂)HCl] | 270/1900 | 100/12 h |
| 15 | 8 | [Ru((R,R)-cyP₂N₂)HCl] | 310/2200 | 100/12 h |
| 16 | 8 | [Ru((R,R)-cyP₂(NH)₂)HCl] | 310/2200 | 100/12 h |

Sub.: substrate: 1) acetone; 2) pivalophenone; 3) pinacolone; 4) N-(phenylmethylidene)-benzenamine; 5) N-(1-phenylethylidene)-benzenamine; (6 N-(phenyl-(2-pyridyl)-methylidene)-benzenamine; 7) 4-phenyl-3-buten-2-one; 8) 5-hexen-2-one
Com/base: complex/base molar ratio in ppm relative to the substrate TABLE 5-continued Comparison of the performances of [Ru((R,R)-cyP₂N₂)HCl] and its [Ru((R,R)-cyP₂(NH)₂)HCl] analogue as catalyst for the hydrogenation of various substrates

| Test | Sub. | Complex | Com/base | Yield/time |
|---|---|---|---|---|

Yield/time = Yield (analyzed by NMR or by isolation) of the corresponding alcohol (namely isopropanol, 2,2-dimethyl-1-phenyl-propanol, 3,3-dimethyl-2-butanol, N-(phenylmethyl)-benzenamine, N-(1-phenylethyl)-benzenamine, N-(phenyl-(2-pyridyl)-methyl)-benzenamine, 4-phenyl-3-buten-2-ol, 5-hexen-2-ol, respectively) after the indicated reaction time in hours.
[a] the product had an ee of 52%

1) [Ru((R,R)-cyP₂N₂)HCl] was obtained according to the following method: 2 ml of tetrahydrofuran were added to a mixture of RuHCl(PPh₃)₃ (300 mg, 0.34 mmol) and (R,R)-cyP₂N₂ (224 mg, 0.34 mmol) and the resulting solution was refluxed. After 1 hour of reflux, under argon, the solution was filtered and 10 ml of hexanes were added to the filtrate, precipitating a brown solid. Yield=243 mg, 90%.
$^1H$-NMR: −14.80 (dd, 1H, RuH, $^2J_{HP}$=35 Hz, $^2J_{HP}$=24 Hz), 0.05–1.39 (m, 8H, CH₂), 2.68 (m, 2H, CH), 6.73–8.51 (m, 30H). $^{31}P\{^1H\}$-NMR: 65.8 (d), 70.9 (d), $^2J_{PP}$=35 Hz.

2) [Ru((R,R)-cyP₂(NH)₂)HCl] was obtained according to the following method: 2 ml of tetrahydrofuran were added to a mixture of RuHCl(PPh₃)₃ (300 mg, 0.34 mmol) and (R,R)-cyP₂(NH)₂ (225 mg, 0.34 mmol) and the resulting solution was refluxed. After 1 hour of reflux, under argon, the solution was filtered and then 10 ml of hexanes were added to the filtrate, precipitating a pale yellow solid. Yield=254 mg, 94%. The NMR spectra indicate the presence of a mixture of isomers.
$^1H$-NMR: −16.79 (dd, $^2J_{HP}$=33 Hz, $^2J_{HP}$=28.8 Hz), −18.08 (dd, $^2J_{HP}$=32.4 Hz, $^2J_{HP}$=32.1 Hz), 0.05–4.85 (m), 6.38–8.60 (m). $^{31}P\{^1H\}$-NMR: 69.9 (d), 63.1 (d), $^2J_{PP}$=32.4 Hz; 65.3 (br), 61.1 (br).

What is claimed is:

1. A process for hydrogenation, using molecular hydrogen ($H_2$), of a C=O or C=N double bond of a substrate, in the presence of a catalytic system, wherein the catalytic system comprises a base and a ruthenium complex with a tetradentate diimino-diphosphine ligand.

2. A process according to claim 1, wherein said ruthenium complex is of formula $$[Ru(P_2N_2)Y_2] \quad (II)$$

in which the Y symbols represent, simultaneously or independently, a hydrogen or halogen atom, a hydroxyl radical, or a $C_1$ to $C_8$ alkoxy or acyloxy radical or other anionic radical, and the ligand $P_2N_2$ represents a tetradentate ligand of formula (III)

in which the dotted lines indicate the position of a C=N double bond;

the R¹ symbols, taken separately, represent simultaneously or independently a linear or branched alkyl or alkenyl group containing 1 to 8 carbon atoms and which is optionally substituted, a cycloalkyl radical or an aromatic ring which is optionally substituted; or two R¹ groups bonded to the same P atom being bonded together to form a ring having 5 to 8 atoms and including the phosphorous atom to which said R¹ groups are bonded;

R², R³ and R⁴, taken separately, represent simultaneously or independently a hydrogen atom, a linear or branched alkyl or alkenyl group containing 1 to 8 carbon atoms and which is optionally substituted, a cycloalkyl radical or an aromatic ring which is optionally substituted; or two adjacent or geminal R² groups optionally being bonded together to form a ring including the carbon atom to which said R² groups are bonded; or an R³ group and an R² group, in α-position to the same N atom, being bonded together to form a ring; or two adjacent R⁴ groups being bonded together to form an aromatic ring;

the indices k are, simultaneously or independently, equal to 0 or 1; and the optional substituents of R¹, R², R³ and R⁴ being halogen atoms or C₁ to C₆ alkyl or alkoxy groups.

3. A process according to claim 2, wherein the ligand P₂N₂ in formula (II) represents a compound of formula

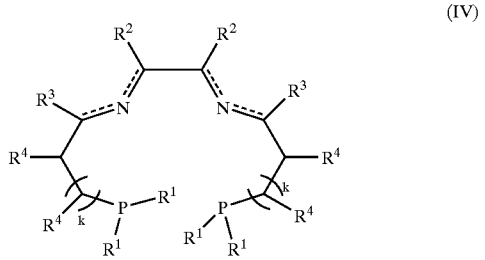

(IV)

wherein the dotted lines indicate the position of a C=N double bond;

the R¹ symbols, taken separately, represent simultaneously or independently a linear or branched alkyl group containing 1 to 4 carbon atoms, a cycloalkyl radical or an aromatic ring which is optionally substituted; or two R¹ groups bonded to the same P atom being bonded together to form a ring having 5 to 6 atoms and including the phosphorous atom to which said R¹ groups are bonded;

R², R³ and R⁴, taken separately, represent simultaneously or independently a hydrogen atom, a linear or branched alkyl group containing 1 to 4 carbon atoms, a cycloalkyl radical or an aromatic ring which is optionally substituted; or two R² groups being bonded together to form a ring including the carbon atom to which said R² groups are bonded; or two adjacent R⁴ groups being bonded together to form an aromatic ring;

the indices k are, simultaneously or independently, equal to 0 or 1; and the optional substituents of the aromatic rings being C₁ to C₄ alkyl or alkoxy groups or fluorine or chlorine atoms.

4. A process according to claim 1, wherein said Ru complex is of formula

[Ru(P₂N₂)Y₂]   (II)

wherein Y represents a hydrogen or chlorine atom, a methoxy, ethoxy or isopropoxy radical, or a CH₃COO or CH₃CH₂COO radical; and the ligand P₂N₂ represents a ligand of the formula

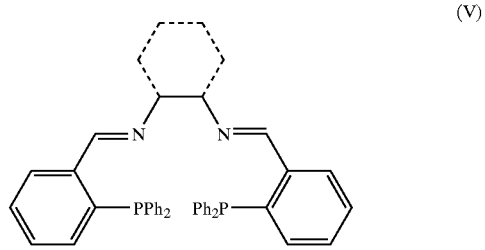

(V)

wherein the dotted lines represent an optional C₆ aliphatic ring and Ph represents a phenyl radical that is optionally substituted with methyl or methoxy groups or fluorine atoms.

5. A process according to claim 1, wherein the substrate is hydrogenated in the presence of a complex prepared in situ and obtainable by reacting an appropriate Ru complex of formula

[Ru("diene")("allyl")₂]

in which "diene" represents a cyclic or linear hydrocarbon containing two carbon-carbon double bonds, conjugated or not, and "allyl" represents a linear or branched C₃ to C₈ hydrocarbon radical containing one carbon-carbon double bond, with a non-coordinating acid, then treating the resulting solution with the desired amount of a ligand N₂P₂, which represents a tetradentate ligand of formula

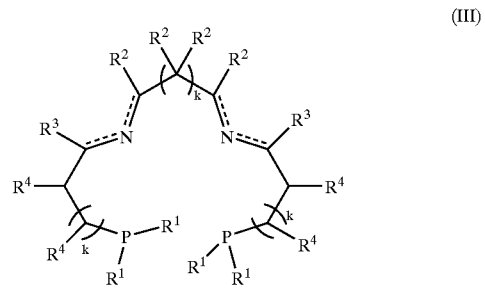

(III)

in which:

the dotted lines indicate the position of a C=N double bond;

the R¹ symbols, taken separately, represent simultaneously or indenendently a linear or branched alkyl or alkenyl group containing 1 to 8 carbon atoms and which is optionally substituted, a cycloalkyl radical or an aromatic ring which is optionally substituted; or two R¹ groups bonded to the same P atom being bonded together to form a ring having 5 to 8 atoms and including the phosphorous atom to which said R¹ groups are bonded;

R², R³ and R⁴, taken separately, represent simultaneously or independently a hydrogen atom, a linear or branched alkyl or alkenyl group containing 1 to 8 carbon atoms and which is optionally substituted, a cycloalkyl radical or an aromatic ring which is optionally substituted; or two adjacent or geminal R² groups optionally being bonded together to form a ring including the carbon atom to which said R² groups are bonded; or an R³ group and an R² group, in α-position to the same N atom, being bonded together to form a ring; or two adjacent R⁴ groups being bonded together to form an aromatic ring;

the indices k are, simultaneously or independently, equal to 0 or 1; and the optional substituents of $R^1$, $R^2$, $R^3$ and $R^4$ being halogen atoms or $C_1$ to $C_6$ alkyl or alkoxy groups, and finally treating the thus obtained mixture with a base in the presence of a primary or secondary alcohol.

6. A process according to claim 5, wherein the [Ru("diene")("allyl")₂] is [Ru(COD)(allyl)₂] or [Ru(COD)(methylallyl)₂].

7. A process according to claim 1, wherein the substrate is hydrogenated in the presence of a complex prepared in situ by reacting a ruthenium complex of formula [Ru(C₆H₆)(Cl)₂]₂ with a required amount of ligand P₂N₂, which represents a tetradentate ligand of formula

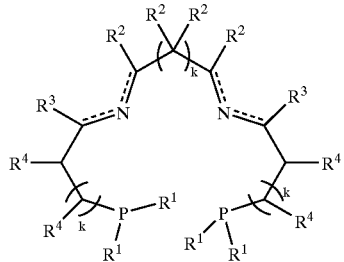

(III)

in which:

the dotted lines indicate the position of a C=N double bond;

the $R^1$ symbols, taken separately, represent simultaneously or independently a linear or branched alkyl or alkenyl group containing 1 to 8 carbon atoms and which is optionally substituted, a cycloalkyl radical or an aromatic ring which is optionally substituted; or two $R^1$ groups bonded to the same P atom being bonded together to form a ring having 5 to 8 atoms and including the phosphorous atom to which said $R^1$ groups are bonded;

$R^2$, $R^3$ and $R^4$, taken separately, represent simultaneously or independently a hydrogen atom, a linear or branched alkyl or alkenyl group containing 1 to 8 carbon atoms and which is optionally substituted, a cycloalkyl radical or an aromatic ring which is optionally substituted; or two adjacent or geminal $R^2$ groups optionally being bonded together to form a ring including the carbon atom to which said $R^2$ groups are bonded; or an $R^3$ group and an $R^2$ group, in α-position to the same N atom, being bonded together to form a ring; or two adjacent $R^4$ groups being bonded together to form an aromatic ring;

the indices k are, simultaneously or independently, equal to 0 or 1; and the optional substituents of $R^1$, $R^2$, $R^3$ and $R^4$ being halogen atoms or $C_1$ to $C_6$ alkyl or alkoxy groups, and then treating the thus obtained reaction mixture with a base, in the presence of an alcohol.

8. A process according to claim 1, wherein the base in the hydrogenation reaction is an organic non-coordinating base, an alkaline or alkaline-earth metal carbonate, a carboxylate salt or an alcoholate or hydroxide salt.

9. A process according to claim 8, wherein the base is an alcoholate or an hydroxide salt selected from the group consisting of the compounds of formula (R⁸O)₂M' and R⁸OM", in which M' is an alkaline-earth metal, M" is an alkaline metal and R⁸ stands for hydrogen or a $C_1$ to $C_6$ linear or branched alkyl radical.

10. A process according to claim 1, wherein there is reduced a substrate of formula

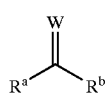

(I)

in which W is an oxygen atom or a NR group, R being a hydrogen atom, a hydroxy radical, a $C_1$ to $C_8$ cyclic, linear or branched alkyl or alkenyl group and which is optionally substituted, or an aromatic ring which is optionally, possibly substituted; and $R^a$ and $R^b$ represent simultaneously or independently a hydrogen, an aromatic group which is optionally substituted, a cyclic, linear or branched alkyl or alkenyl group which is optionally substituted, or a heterocyclic group which is optionally substituted; or two of symbols $R^a$, $R^b$ and R taken together form a ring which is optionally substituted;

the possible substituents of $R^a$, $R^b$ and R being halogen atoms, $OR^c$, $NR^c_2$ or $R^c$ groups, in which $R^c$ is a hydrogen atom or a $C_1$ to $C_{10}$ cyclic, linear or branched alkyl or alkenyl group, to provide the corresponding hydrogenated compound of formula

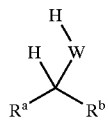

(I')

wherein W, $R^a$ and $R^b$ are defined as in formula (I).

11. A process according to claim 10, wherein there is hydrogenated a substrate of formula

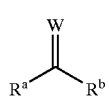

(I)

in which W is an oxygen atom and $R^a$, $R^b$ are defined as in claim 10.

12. A process according to claim 10, wherein there is hydrogenated a substrate of formula

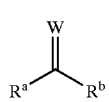

(I)

in which W is a NR group and $R^a$, $R^b$ and R are defined as in claim 10.

13. A process according to claim 1, wherein the hydrogenation is carried out in the absence of a solvent.

14. A process according to claim 1, wherein the hydrogenation is carried out in a primary or secondary alcohol as a solvent.

15. A process according to claim 14, wherein the solvent is ethanol or isopropanol.

16. A process according to claim 5, wherein the base used to treat the mixture is an organic non-coordinating base, an alkaline or alkaline-earth metal carbonate, a carboxylate salt or an alcoholate or hydroxide salt.

17. A process according to claim 16, wherein the base is an alcoholate or an hydroxide salt selected from the group consisting of the compounds of formula $(R^8O)_2M'$ and $R^8OM''$, in which M' is an alkaline-earth metal, M'' is an alkaline metal and $R^8$ stands for hydrogen or a $C_1$ to $C_6$ linear or branched alkyl radical.

18. A process according to claim 7, wherein the base used to treat the mixture is an organic non-coordinating base, an alkaline or alkaline-earth metal carbonate, a carboxylate salt or an alcoholate or hydroxide salt.

19. A process according to claim 18, wherein the base is an alcoholate or an hydroxide salt selected from the group consisting of the compounds of formula $(R^8O)_2M'$ and $R^8OM''$, in which M' is an alkaline-earth metal, M'' is an alkaline metal and $R^8$ stands for hydrogen or a $C_1$ to $C_6$ linear or branched alkyl radical.

* * * * *

UNITED STATES PATENT AND TRADEMARK OFFICE
CERTIFICATE OF CORRECTION

PATENT NO. : 6,878,852 B2
DATED : April 12, 2005
INVENTOR(S) : Rautenstrauch et al.

It is certified that error appears in the above-identified patent and that said Letters Patent is hereby corrected as shown below:

Title Page,
Item [22], PCT Filed, change "Nov. 11, 2001" to -- Nov. 16, 2001 --.
Item [56], References Cited, FOREIGN PATENT DOCUMENTS, after "1 120 162 A2", change "12/1997" to -- 8/2001 --.
OTHER PUBLICATIONS,
After "Abstract–XP002175802," delete "Jingxing et al." and insert -- Gao et al. --; and delete "STN 2000" and insert -- (2000) --.
After "Abstract–XP002175800," delete "Wai-Kwok et al." and insert -- Wong et al. --; and after "trans-RuC12(1R, 2R-cyclohexyl-" delete "P2N2.cntdot, STN 1996" and insert -- $P_2N_2$·$C_6H_5CH_3$ (1996) --.
After "Abstract–XP002175801," delete "Pinapian et al." and insert -- Xu et al. --; and delete "STN 1997" and insert -- (1997); --.
After "Abstract–XP002175803," delete "Jingxing et al." and insert -- Gao et al. --; and after "ruthenium (I) ceomplexes" delete "retrieved from STN 1995" and insert -- (1995) --.
After "Abstract–XP002175805," delete "Jingxing et al." and insert -- Gao et al. --; and after "for reduction of ketones" delete "retrieved from STN 2000" and insert -- (2000) --.
After "Abstract–XP002175804," delete "Jingxing et al." and insert -- Gao et al. --; and after "ruthenium complexes with aminophosphine ligands," delete "retrieved from STN 1999" and insert -- (1999) --.
After "Abstract–XP002175799," delete "Jingxing et al." and insert -- Gao et al. --; after "catalysis hydrogenation of," delete "functional zed" and insert -- functionalized --; and change "1995" to -- (1995) --.

Column 12,
Line 51, change "indenendently" to -- independently --.

Signed and Sealed this

Twelfth Day of July, 2005

JON W. DUDAS
*Director of the United States Patent and Trademark Office*